(12) United States Patent
Bornzin et al.

(10) Patent No.: US 8,649,865 B2
(45) Date of Patent: Feb. 11, 2014

(54) METHOD AND SYSTEM FOR HEMODYNAMIC OPTIMIZATION USING PLETHYSMOGRAPHY

(75) Inventors: Gene A. Bornzin, Simi Valley, CA (US); Wenbo Hou, Lancaster, CA (US); Edward Karst, South Pasadena, CA (US); Brian J. Wenzel, San Jose, CA (US); Timothy A Fayram, Gilroy, CA (US)

(73) Assignee: Pacesetter, Inc., Sylmar, CA (US)

( * ) Notice: Subject to any disclaimer, the term of this patent is extended or adjusted under 35 U.S.C. 154(b) by 315 days.

(21) Appl. No.: 12/964,625

(22) Filed: Dec. 9, 2010

(65) Prior Publication Data

US 2011/0144711 A1  Jun. 16, 2011

Related U.S. Application Data

(60) Provisional application No. 61/285,321, filed on Dec. 10, 2009.

(51) Int. Cl.
*A61N 1/00* (2006.01)

(52) U.S. Cl.
USPC ................................. 607/18; 607/17; 607/119

(58) Field of Classification Search
USPC ............................... 607/17–18, 119
See application file for complete search history.

(56) References Cited

U.S. PATENT DOCUMENTS

2006/0247698 A1* 11/2006 Burnes et al. .................... 607/9
2008/0294218 A1* 11/2008 Savage et al. .................. 607/30

* cited by examiner

*Primary Examiner* — Nicole F Lavert

(57) ABSTRACT

Time delays between a feature of a signal indicative of electrical activity of a patient's heart and a feature of a plethysmograph signal indicative of changes in arterial blood volume are used to arrange the operation of an implantable device, such as a pacemaker. Shorter time delays between the feature of the signal indicative of electrical activity of a patient's heart and the feature of the plethysmograph signal indicative of changes in arterial blood volume are indicative of larger cardiac stroke volumes. The time delay can be used to select a pacing site or combination of pacing sites and/or to select a pacing interval set.

18 Claims, 9 Drawing Sheets

Scatter plots of PPG time features vs. LV standard hemodynamics

US 8,649,865 B2

METHOD AND SYSTEM FOR HEMODYNAMIC OPTIMIZATION USING PLETHYSMOGRAPHY

PRIORITY CLAIM

This application claims priority under 35 U.S.C. 119(e) to U.S. Provisional Patent Application No. 61/285,321, filed Dec. 10, 2009, entitled "Method and System for Hemodynamic Optimization during Cardiac Resynchronization by Photoplethysmography," which is incorporated herein by reference.

FIELD OF THE INVENTION

The invention generally relates to implantable medical devices (IMDs), such as pacemakers, implantable cardioverter/defibrillators (ICDs), and cardiac resynchronization therapy device/defibrillators (CRT-Ds) and, in particular, to techniques and systems for optimizing the hemodynamic performance of these devices using plethysmography signals.

BACKGROUND OF THE INVENTION

Intra-operative cardiac resynchronization therapy (CRT) optimization has been demonstrated to significantly improve hemodynamics and will likely improve outcomes of heart failure (HF) patient's undergoing CRT implant. It is believed that patient selection, pacing site, and device timing settings can affect the optimization outcomes.

Currently, the Millar blood pressure sensor is considered as the gold standard for academic related hemodynamic measurement. The Millar blood sensor, however, is invasive and risky. Echocardiography is another approach that is used in clinical practice, but its reliability and accuracy have raised many concerns recently. Echocardiography is also slow and cumbersome when performing a sterile implant. Both the Millar blood pressure sensor and echocardiography have their own technical limitations for CRT application. Therefore, there is no simple and reliable clinical tool for monitoring and optimizing hemodynamics during CRT.

Methods for CRT optimization using photoplethysmography (PPG) have been previously described. U.S. Pat. No. 7,177,686, (Turcott), entitled "Using Photo-Plethysmography to Monitor Autonomic Tone and Performing Pacing Optimization Based on Monitored Autonomic Tone" discloses CRT hemodynamic optimization using a hypothesized stroke volume surrogate, which relates to using amplitude of PPG signal during different pacing intervals. U.S. Pat. No. 6,871,088, entitled "Method and Apparatus for Optimizing Cardiac Resynchronization Therapy" and U.S. Pat. No. 7,548,784, entitled "Method and Apparatus for Optimizing Cardiac Resynchronization Therapy" (both Chinchoy), describe hemodynamic optimization by a cardiac output method, which again uses amplitude features of the PPG signal or a surrogate for blood pressure in order to estimate stroke volume.

SUMMARY

Embodiments of the present invention use time delays between a feature of a signal indicative of electrical activity of a patient's heart and a feature of a plethysmograph signal indicative of arterial blood volume changes to arrange the operation of an implantable device, such as a pacemaker. Shorter time delays between the feature of the signal indicative of electrical activity of a patient's heart and the feature of the plethysmograph signal indicative of arterial blood volume changes indicate larger cardiac stroke volumes. By monitoring such time delays associated with different arrangements of the implantable device, the cardiac stroke volume can be ensured to be sufficient.

In one embodiment, the time delays are used to select a pacing site or a combination of pacing sites used for cardiac pacing by an implantable medical device. Different pacing sites and combinations of pacing sites will have different associated time delays and these time delays can be used to select a pacing site or combination of pacing sites.

In another embodiment, the time delays are used to select a pacing interval parameter set for an implantable medical device. Different pacing interval parameter sets will have different associated time delays and these associated time delays can be used to select a pacing interval parameter set.

Additional and alternative embodiments, features and advantages of the invention will appear from the following description in which the preferred embodiments have been set forth in detail, in conjunction with the accompanying drawings and claims.

DETAILED DESCRIPTION OF THE PREFERRED EMBODIMENTS

Figure 1A:
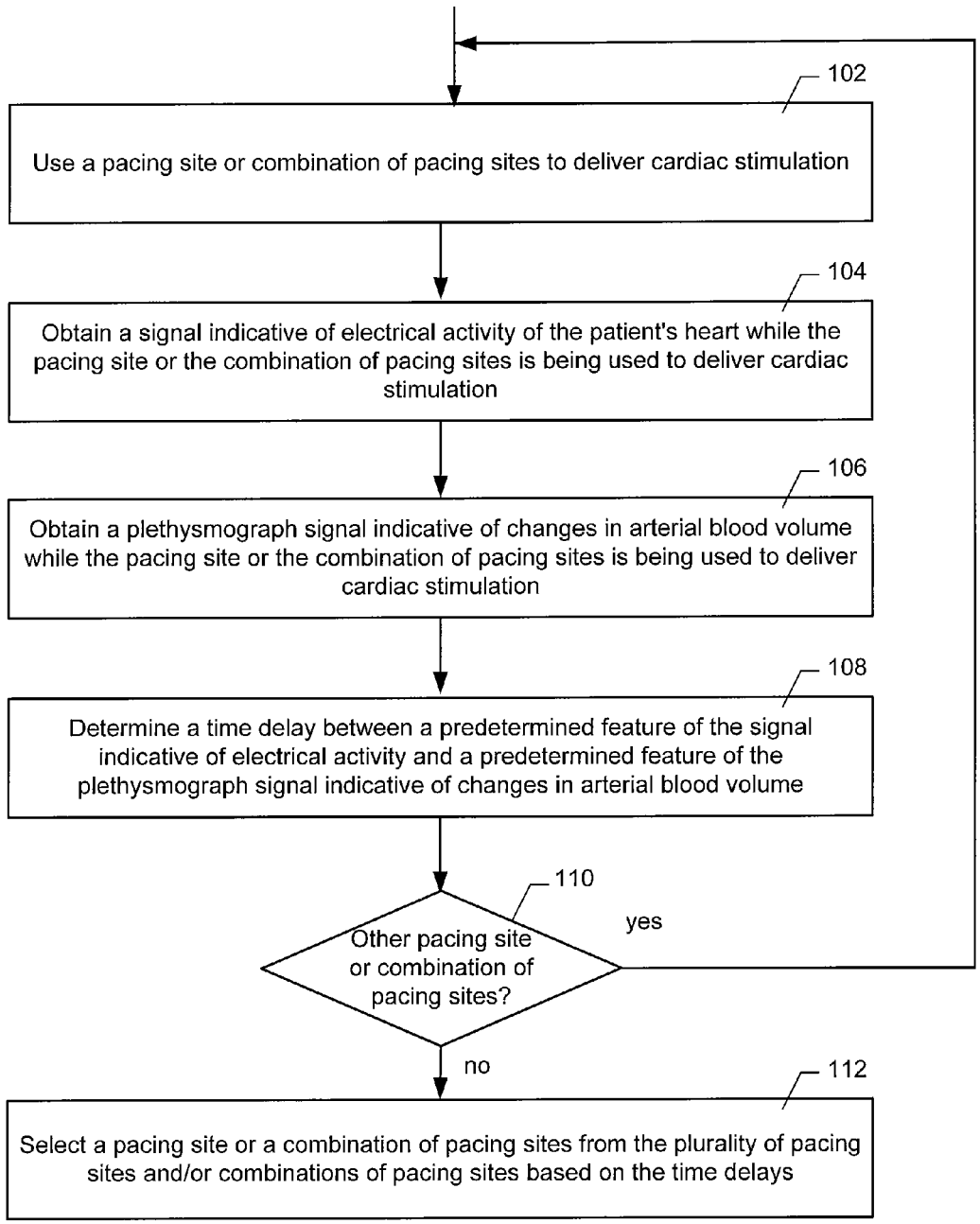
FIG. 1A is a high level flow diagram illustrating the selection of a pacing site or combination of pacing sites based on time delays between features of a signal indicative of electrical activity of a patient's heart and features of a plethysmograph signal indicative of arterial blood volume changes.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

It would be apparent to one of skill in the art that the present invention, as described below, may be implemented in many different embodiments of hardware, software, firmware, and/or the entities illustrated in the figures. Any actual software, firmware and/or hardware described herein is not limiting of the present invention. Thus, the operation and behavior of the present invention will be described with the understanding that modifications and variations of the embodiments are possible, given the level of detail presented herein.

The high level flow diagram of FIG. 1A will now be used to explain various embodiments of the present invention that can be used to select a pacing site or combination of pacing sites using a time delay between a feature of a signal indicative of electrical activity of a patient's heart and a feature of a plethysmograph signal. Such a selection of the pacing sites or combination of pacing sites can be done interoperatively to select the pacing site or combination of pacing sites during surgery to implant the implantable device. Alternatively, a multielectrode lead can be used and the selection of the pacing sites or combination of pacing sites can be done after the implantable device has been implanted. Such embodiments can be implemented by an implantable system, examples of which are discussed below with reference to FIGS. 3 and 4. In FIG. 1A and the other flow diagrams described herein, the various algorithmic steps are summarized in individual 'blocks'. Such blocks describe specific actions or decisions that are made or carried out as the algorithm proceeds. Where a microcontroller (or equivalent) is employed, the flow diagram presented herein provides the basis for a 'control program' that may be used by such a microcontroller (or equivalent) to effectuate the desired control of the implantable system. Those skilled in the art may readily write such a control program based on the flow diagram and other descriptions presented herein.

Referring to FIG. 1A, at step 102, a pacing site or combination of pacing sites is used to deliver cardiac stimulation. The cardiac stimulation can be delivered to provide cardiac resynchronization therapy (CRT) or other cardiac therapy. The plurality of pacing sites and/or combination of pacing sites can be obtained by moving one or more electrodes interoperatively. Alternatively, a multielectrode lead can be used to select different pacing sites and/or combinations of pacing sites.

In step 104, a signal indicative of electrical activity of the patient's heart is obtained while the pacing site or combination of pacing sites is used to deliver cardiac stimulation or other cardiac therapy. The signal indicative of electrical activity of the patient's heart can be an intercardiac electrogram (IEGM), a subcutaneous electrocardiogram (subQ ECG), a surface electrocardiogram (surface ECG), a timing signal for the cardiac stimulation provided by the implantable device, or some other signal.

When the method of FIG. 1A is done interoperatively, the number of pacing sites or combination of pacing sites is preferably kept relatively small. The various different pacing sites can be, e.g., within a specific coronary branch, such as the posterolateral vein, or within different branches. The pacing electrode(s) for a pacing site or combination of pacing sites can be entered, e.g., through the coronary sinus to the posterolateral vein. If a pacing site or combination of pacing sites in the posterolateral vein are insufficient as tested using the time delays, other locations such as the anterolateral vein or the lateral vein can be used. In an embodiment, an X-ray of the veins (venogram) is done to identify candidate locations for the pacing site or combination of pacing sites. The pacing electrode(s) is/are then positioned in the candidate locations one-by-one and tested using the time delay method described above until sufficient improvement resulting from the pacing intervention is found.

In step 106, a plethysmograph signal indicative of changes in arterial blood volume is obtained while the pacing site or combination of pacing sites is used to deliver cardiac stimulation. The signal indicative of changes in arterial blood volume obtained at step 104 can be a photoplethysmography (PPG) signal, an impedance plethysmograph (IPG) signal, or some other plethysmography signal. An optical sensor can be used to obtain a PPG signal, or implanted electrodes can be used to obtain an IPG signal.

The plethysmograph sensor can be either noninvasive or implantable. The plethysmography signal can be obtained using a plethysmograph sensor that is at least 1 cm remote from the pacing site or combination of pacing sites. In one example, during implant of the IMD, a noninvasive PPG sensor can be attached to the patient, e.g. to a forehead, toe, finger or earlobe, and connected to a data acquisition interface. For an implantable PPG sensor, the sensor may be implanted, e.g., in the patient's pectoral pocket if it is incorporated in to an IMD, such as described in U.S. Pat. Appl. Pub. No. 2009/0062667 (Fayram et al.), now U.S. Pat. No. 8,147,416, entitled "Implantable Systemic Blood Pressure Measurement Systems and Methods" which is incorporated herein by reference. A real time PPG waveform can be displayed on a monitor and time features of PPG waveforms can be extracted simultaneously.

In still other embodiments, the plethysmography signal indicative of changes in arterial blood volume can be a signal output by a sensor including a piezo-electric diaphragm. Alternative sensors that can be used to produce the plethysmography signal indicative of changes in arterial blood volume, include, but are not limited to, a close range microphone, a sensor including a small mass on the end of a piezo bending beam with the mass located on the surface of a small artery, a transmission mode infrared motion sensor sensing across the surface of a small artery, or a MEMS accelerometer located on the surface of a small artery. Such alternative sensors can be located, e.g., on the tip of a short lead connected to a device that is subcutaneously implanted. Such an implanted sensor can be close to the patient's aorta. For example, the implanted sensor (used to obtain the signal indicative of changes in arterial blood volume) can be 10 mm from the patient's aortic root. Such a sensor can be implanted, e.g., in the pectoral region of a patient. An alternative location for implantation of the sensor includes, but is not limited to, the patient's abdominal region. For the remainder of this discussion, it will be assumed that the plethysmography signal is a PPG or IPG signal, which is collectively referred to as a PPG/IPG signal. However, as just explained above, alternative plethysmography signals can be used.

In step 108, a time delay between a predetermined feature of the signal indicative of electrical activity of the patient's heart and a predetermined feature of the plethysmography signal indicative of arterial blood volume changes is determined. The predetermined feature of the signal indicative of electrical activity can be an R-wave, a Q-wave, the QRS complex, a pacing timing signal feature or some other feature. The predetermined feature of the signal indicative of electrical activity can be indicative of ventricular depolarization or some other cardiac event.

The predetermined feature of the plethysmography signal indicative of changes of arterial blood volume can be a minimum amplitude, a maximum upward slope, a maximum amplitude, a maximum downward slope, a dicrotic notch or some other feature.

In accordance with an embodiment, a wavelet transformation can alternatively be used to detect predetermined features of the signals. Wavelet transformation techniques are well known, and thus need, not be described herein.

In step 110, it is checked if there is any additional pacing site or combination of pacing sites to test. If so, steps 102, 104, 106, 108 and 110 are repeated. After all of the pacing sites or combinations of pacing sites have been tested, a pacing site and/or combination of pacing sites is selected from the plurality of tested pacing sites and/or combinations of pacing sites based on the time delays in step 112. In accordance with an embodiment, it is desired to have as short as possible of a time delay between the feature of the signal indicative of electrical activity of the patient's heart and the feature of the plethysmograph signal indicative of changes in arterial blood volume. Such a time delay shortens with increased stroke volume. This is because a transient increase in stroke volume causes the arteries to distend, which makes them less compliant. This means that a pressure wave entering the aorta as a result of a systolic contraction will then traverse the arteries more quickly on its path to the plethysmography (e.g., PPG) sensor site.

In one embodiment, the pacing site or the combination of pacing sites that corresponds to the shortest of the time delays is selected. Alternatively, the pacing site or the combination of pacing sites that corresponds to the shortest of the time delays at which phrenic nerve stimulation did not occur can be selected.

In another embodiment, the pacing site or the combination of pacing sites that corresponds to any one of the time delays that meet a predetermined criterion is selected. For example, pacing sites and/or combinations of pacing sites can be tested until a pacing site or a combination of pacing sites has a time delay that is shorter than a threshold. This can be especially useful when the method is done interoperatively since it is undesirable to spend too much time testing the pacing sites or repositioning the pacing electrode during surgery.

While the selection of the pacing site or combination of pacing sites is based on the time delay, the selection may also be based on additional factors as well. For example, the pacing site or combination of pacing sites can be selected based on a function using both the time delay and an amplitude of the plethysmograph signal indicative of changes in arterial blood volume. Larger amplitudes of the plethysmograph signal indicate larger cardiac stroke volumes.

Figure 1B:
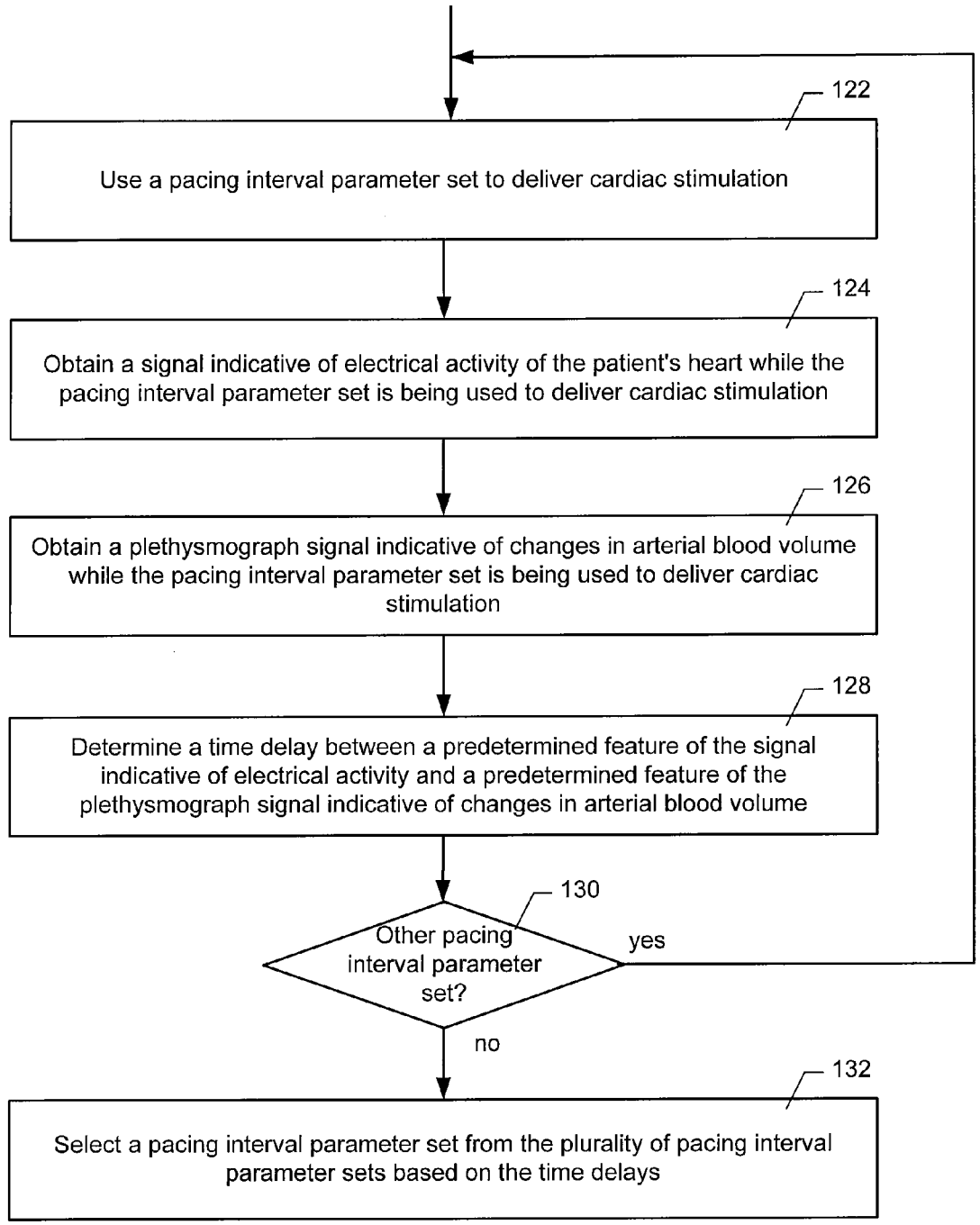
FIG. 1B is a high level flow diagram illustrating the selection of a pacing interval parameter set based on time delays between features of a signal indicative of electrical activity of a patient's heart and features of a plethysmograph signal indicative of arterial blood volume changes.

The high level flow diagram of FIG. 1B will now be used to explain various embodiments of the present invention that can be used to select a pacing interval parameter set using a time delay between a feature of a signal indicative of electrical activity of a patient's heart and a feature of a plethysmograph signal indicative of changes in arterial blood volume. The pacing interval parameter set can include one or more pacing parameters. The pacing interval parameter sets can have an initiating event of a delivered pacing pulse or a sensed depolarization.

The pacing interval parameter sets can include one or more pacing interval parameters, such as but not limited to, atrioventricular (AV) delay, interventricular (VV) delay, interatrial (AA) delay, and intraventricular delay. The intraventricular delay can be between multiple pacing pulses in the same chamber.

In step 122, a pacing interval parameter set is used to deliver cardiac stimulation. The cardiac stimulation can be delivered to provide cardiac resynchronization therapy or other cardiac therapy. The cardiac stimulation can be provided by an implantable device, such as a pacemaker.

In step 124, a signal indicative of electrical activity of the patient's heart is obtained while the pacing interval parameter set is used to provide cardiac stimulation. The signal indicative of electrical activity can be an intracardiac electrogram (IEGM), a subcutaneous electrocardiogram (subQ ECG), a surface electrocardiogram (surface ECG), a timing signal for the cardiac stimulation provided by the implantable device, or some other signal.

In step 126, a plethysmograph signal indicative of changes in arterial blood volume is obtained while the pacing interval parameter set is used. The plethysmograph signal indicative of changes in arterial blood volume can be a PPG signal, an IPG signal, or some other plethysmograph signal, examples of which were discussed above with reference to step 106 of FIG. 1A.

In step 128, a time delay between a predetermined feature of the signal indicative of electrical activity of the patient and a predetermined feature of the plethysmograph signal indicative of changes in arterial blood volume is determined. Exemplary predetermined features of the signal indicative of electrical activity and of the plethysmograph signal indicative of changes of arterial blood volume were discussed above with respect to step 108 of FIG. 1A.

In step 130, it is checked if there is any additional pacing interval parameter set to test. If so, steps 122, 124, 126, 128 and 130 are repeated. After all of the pacing interval parameter sets are tested, a pacing parameter set is selected based on the time delays in step 132.

In one embodiment, the pacing interval parameter set that corresponds to the shortest of the time delays is selected. Alternatively, the pacing interval parameter set that corresponds to the shortest of the time delays at which phrenic nerve stimulation does not occur is selected.

In one embodiment, any one of the pacing interval parameter sets with a time delay that meets a predetermined criterion is selected. For example, the pacing interval parameter sets can be tested until a tested pacing interval parameter set has a time delay that is shorter than a threshold.

In one embodiment, the time delays are one of multiple factors that are used in selecting a pacing parameter set for use. In other words, the selection is based on the time delays in combination with other factors. For example, a pacing interval set can be selected based on a function using both the time delay and an amplitude of the plethysmograph signal indicative of changes in arterial blood volume.

Embodiments of the present invention are not limited to the exact order and/or boundaries of the steps shown in FIGS. 1A and 1B. In fact, many of the steps can be performed in a different order than shown, and many steps can be combined, or separated into multiple steps. For another example, certain steps shown in the FIGS. 1A and 1B can be separated into two or more steps. The time order is only important where a step acts on the results of a previous step.

Figure 2A:
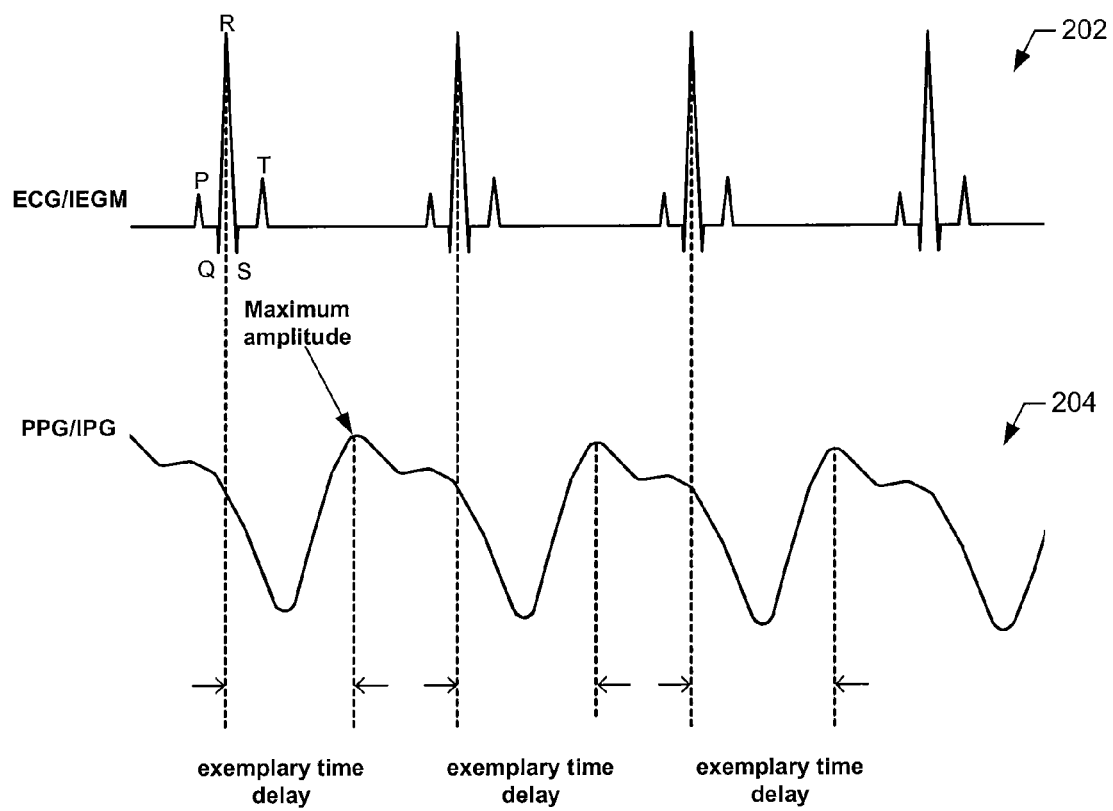
FIG. 2A is a diagram including exemplary signal waveforms that are used to show the relative timing of various signals, and how an exemplary time delay can be determined in accordance with an embodiment of the present invention.

Referring to FIG. 2A, the representative signal waveforms therein are used to show the relative timing of a signal indicative of electrical activity of a patient's heart and a plethysmograph signal indicative of changes in arterial blood volume. The upper most waveform is representative of an electrocardiogram (ECG) or intracardiac electrogram (IEGM) signal 202 (collectively referred to as ECG/IEGM signal 202), which is indicative of electrical activity of the patient's heart. As discussed above, a pacing timing signal could also be used. The following waveform is representative of a photoplethysmography (PPG) signal or impedance plethysmography signal (IPG) 204, both of which are indicative of changes in arterial blood volume.

Referring to the ECG/IEGM signal 202, each cycle of the signal 202 is shown as including a P wave, a QRS complex (including Q, R and S waves) and a T wave. The P wave is caused by depolarization of the atria. This is followed by atrial contraction, during which expulsion of blood from the atrium results in further filling of the ventricle. Ventricular depolarization, indicated by the QRS complex, initiates contraction of the ventricles resulting in a rise in ventricular pressure until it exceeds the pulmonary and aortic diastolic blood pressures to result in forward flow as the blood is ejected from the ventricles. Ventricular repolarization occurs thereafter, as indicated by the T wave and this is associated with the onset of ventricular relaxation in which forward flow stops from the ventricles into the aorta and pulmonary arteries. Thereafter, the pressure in the ventricles falls below that in the atria at which time the mitral and tricuspid valves open to begin to passively fill the ventricles during diastole.

Figure 2B:
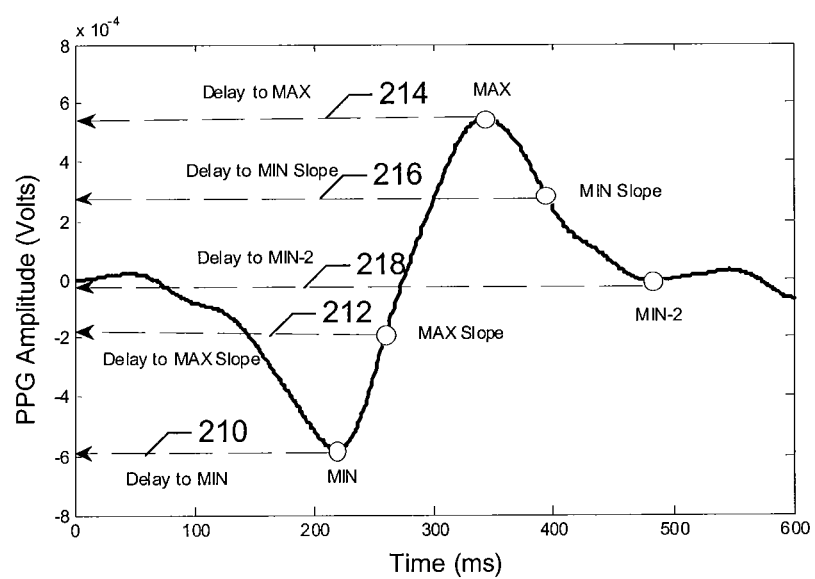
FIG. 2B is a diagram that depicts a plethysmograph amplitude as a function of time that shows various time delays from a cardiac polarization event to plethysmograph waveform features.

As illustrated in FIG. 2A, the time delay can be a time delay from an R-wave of the ECG/IEGM 202 to a maximum amplitude of the PPG/IPG signal 204. FIG. 2B illustrates other exemplary time delays from an R wave to a feature of the plethysmograph signal. These time delays include a time delay 210 from the R wave to the minimum (pulse foot), a time delay 212 from the R wave to the maximum slope, a time delay 214 from the R wave to the maximum, a time delay 216 from the R wave to the minimum slope 216, and a time delay 218 from the R wave to the second minimum (i.e., a dicrotic notch).

The time delay can be determined by determining a time from a detected predetermined feature of a signal indicative of electrical activity of a patient's heart to detect predetermined features of the plethysmograph signal indicative of arterial blood volume changes. In accordance with certain embodiments, the predetermined feature of the signal indicative of electrical activity of a patient's heart and/or the predetermined feature of the plethysmograph signal indicative of arterial blood volume changes can be determined using a wavelet transformations. The wavelet transformation provides a consistent and robust technique to detect the predetermined features used in determining the time delay.

The time delays can be individual time delays or average time delays constructed using multiple time delay values over a window of time.

When a multi-electrode lead is used, pacing sites or combinations of pacing sites can be tested from time to time to select a current preferred pacing site or current combination of pacing sites. The one or more electrodes of the multi-electrode lead that correspond to the current preferred pacing site or the current preferred combination of pacing sites can be selected for stimulation delivery. From time to time, as the phrase is used herein, can be periodically (e.g., once per day, week, month) or aperiodically (e.g., in response to a triggering event, such as detected indications of weakening cardiac function, but is not limited thereto).

The elapsed time delay from an electrical activation, as indicated by an R wave, and appearance of a pressure pulsation at the PPG sensor site correlates to systolic blood pressure (See, for example, U.S. Pat. App. Pub. No. 2009/0062667, which was incorporated herein by reference above). Hemodynamic experimental results on Left Bundle Branch Block (LBBB) Heart Failure (HF) canine models show that there exists strong correlation between PPG time features with max left ventricular (LV) dp/dt, max LV pressure (which is equal to systolic blood pressure) and cardiac output. Exemplary calculated correlation coefficients are listed in Table 1.

TABLE 1

Correlation between LV pressure and PPG time features.

| Standard Hemodynamics | Delay to PPG Max Amp. | Delay to PPG Min Amp. | Delay to PPG Max slope | Delay to PPG Min slope |
|---|---|---|---|---|
| Max LV dp/dt | 0.90 | 0.90 | 0.83 | 0.77 |
| Max LVP | 0.93 | 0.89 | 0.90 | 0.82 |
| Cardiac Output | 0.82 | 0.83 | 0.85 | 0.84 |

Figure 5:
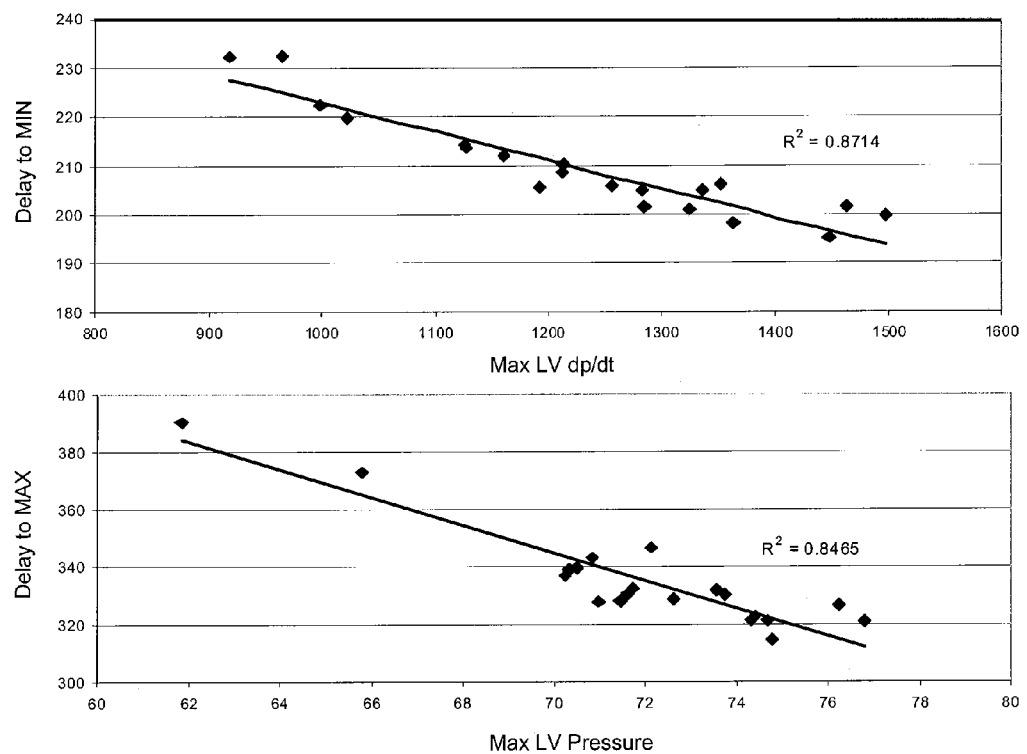
FIG. 5 is a diagram that includes a top representative scatter plot between a PPG based measurement (polarization time delay to PPG minimum amplitude) and a standard hemodynamic measurement (Left Ventricle (LV) maximum dp/dt) and bottom scatter plot between another PPG based measurement (polarization time delay to PPG maximum amplitude) and another standard hemodynamic measurement (maximum LV pressure).

With reference to FIG. 5, data collected during testing in a LBBB HF canine model evidences a strong correlation between PPG based time features and standard hemodynamics measurements. For example, as shown in the top plot, the time delay between a polarization event and the minimum amplitude of a PPG signal corresponds to maximum LV dp/dt at various different pacing interventions. As evidenced in the bottom plot, a similar strong correlation exists between the time delay of a polarization event and the maximum amplitude of a PPG signal and maximum LV pressure.

Figure 6:
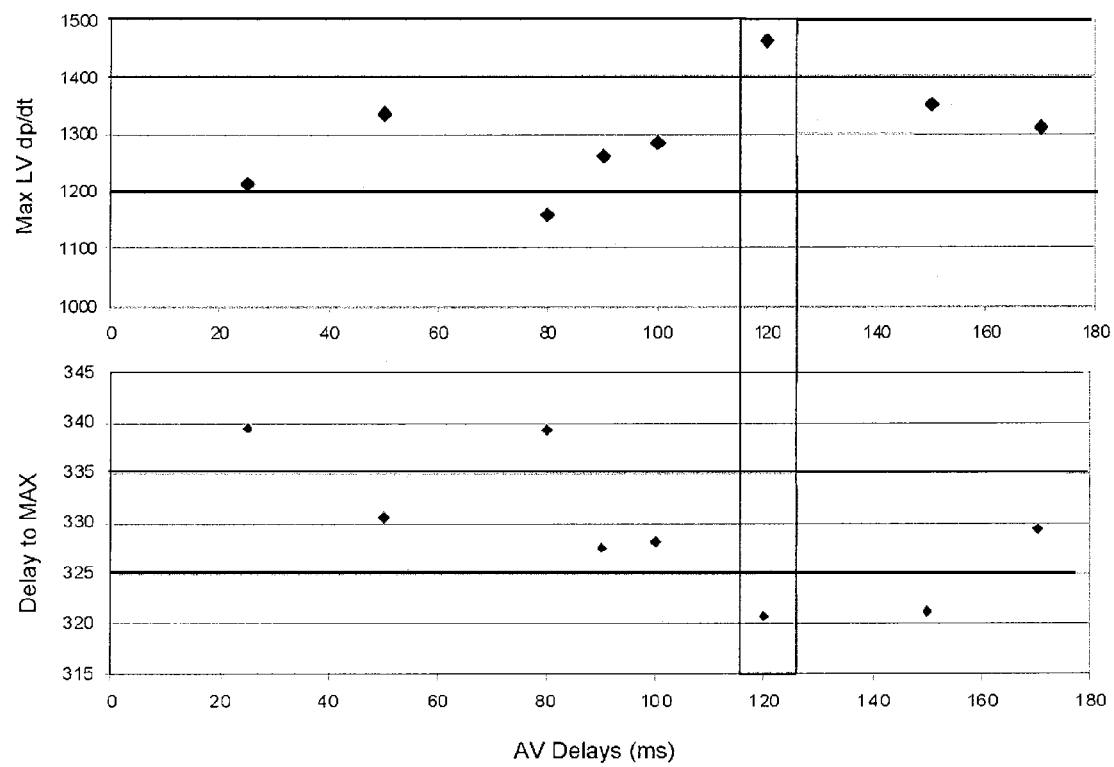
FIG. 6 is a diagram that includes a top plot depicting standard hemodynamic measurements (LV dp/dt) obtained at different AV delay pacing interventions and a bottom plot depicting corresponding PPG based measurements (polarization time delay to PPG maximum amplitude) obtained at the same atrioventricular (AV) delay pacing interventions as the top plot.

FIG. 6 further shows the feasibility for using a PPG sensor to optimize IMD settings for optimized CRT. From these plots it is noted that when LV dp/dt reaches a maximum at an atrioventricular (AV) delay of 120 ms, the PPG based time feature, time delay to maximum amplitude of PPG, is also at the minimum as shown in the plot. This is because the time delay to maximum amplitude of PPG is inversed to LV max dp/dt.

Figure 7:
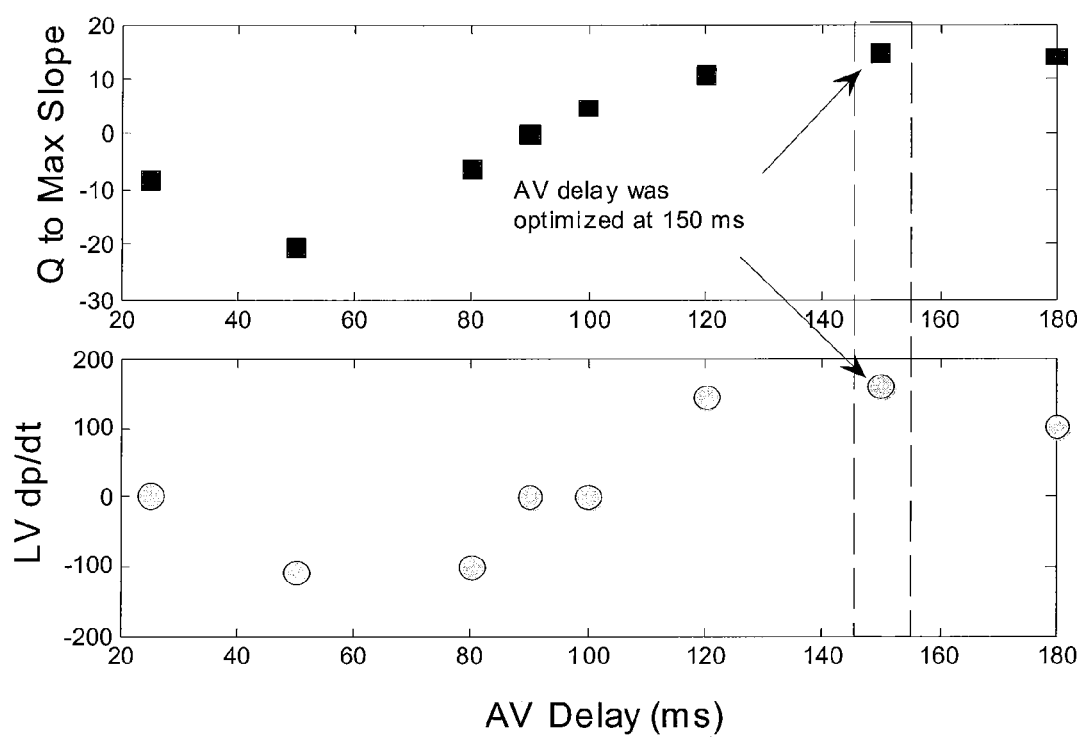
FIG. 7 is a diagram that includes a top plot depicting PPG based measurements (polarization time delay to PPG maximum slope) obtained at different AV delay pacing interventions and a bottom plot depicting corresponding standard hemodynamic measurements (LV dp/dt) obtained at the same AV delay pacing interventions as the top plot.

FIG. 7 presents results from a canine study described below. Six canines with HF, created by left bundle branch (LBB) ablation and rapid right ventricular (RV) pacing, were implanted with standard right arterial (RA), right ventricular (RV), and left ventricular (LV) cardiac resynchronization therapy defibrillator (CRT-D) leads. PPG signals were obtained using a Nellcor tongue sensor. Pressure catheters (Millar Instruments, SPC-340) were placed in the Left Ventricular (LV) and Cardiac Output (CO) was measured using the Fick method. Dual pacing only (DOO)-biventricular (BiV) simultaneous pacing at 90 ms was used as control prior to each test maneuver. Signals were recorded and later processed. The correlation coefficient was calculated and averaged across all animals.

The results of the study are as follows. PPG features correlate well with standard hemodynamics. During atrioventricular (AV) delay optimization, correlation between Q wave to max PPG slope (Q-max) and CO is 0.78 while correlation between PPG amplitude and LV dP/dt was 0.74 for DOO BiV pacing. There was perfect agreement between optimal AV delay determined by CO and Q-max in five of five subjects. There was perfect agreement between LV dP/dt and PPG amplitude observed in four of six subjects while the other two subjects' AV delays were within 10 and 30 ms. FIG. 7 shows LV dP/dt and Q-Max are optimized simultaneously at an AV delay (AVD) of 150 ms, demonstrating Q-Max can be used as a LV dP/dt surrogate for AV delay optimization.

Based on the correlations discovered during the foregoing canine studies, an algorithm based on PPG sensor measurements may be used during implant of an IMD, during follow-up, or periodically (in the case of implanted PPG sensors) to optimize CRT. Examples of such algorithms were discussed above with reference to FIGS. 1A and 1B.

In one configuration, pacing site optimization may be performed during implant or at follow-up in the case of a multi-electrode IMD system with electronic repositioning. In either case, for each of a plurality of electrode placement locations within a patient, an electrode at that location is used to obtain a signal indicative of electrical activity of the patient's heart and a plethysmography sensor is used to obtain a signal indicative of changes in arterial blood volume. A processor can calculate the time between a polarization event, e.g., R wave, Q onset, within the electrical activity signal and a feature of the plethysmography signal, e.g., the maximum amplitude, the minimum amplitude, the maximum slope or the minimum slope, and can compare the plurality of calculated times. The electrode location corresponding to the minimum time delay can be selected as the optimal electrode location, in accordance with an embodiment.

Once the optimal electrode location is determined, the algorithm may proceed with pacing intervention optimization. In this case, for each of a plurality of pacing interventions, the electrode placed at the optimal location is used to obtain a signal indicative of electrical activity of the patient's heart. Likewise, the plethysmography sensor is used to obtain a signal indicative of changes in arterial blood volume. The processor then calculates the time between the polarization event within the electrical activity signal and a feature of the plethysmography signal and compares the plurality of calculated times. The intervention corresponding to the minimum time delay can be selected as the optimal pacing intervention.

In another embodiment of the invention estimates of blood pressure changes and/or dP/dt changes are used to estimate hemodynamics. Blood pressure measured with a sphygmomanometer may be used to calibrate the plethysmography timing signals. Combinations of the PPG timing signals may be used to create a more robust estimate of the blood pressure and dP/dt. Furthermore this embodiment includes the potential of using waveform morphology, as well as amplitude information, from the PPG to estimate hemodynamics.

In specific embodiments, an automated measurement system automatically changes pacing regimens for comparison. The pacing interval parameter set can be switched between control values and the pacing interval parameters set under test. For instance, single chamber atrial pacing (AAI) at 80 ppm (or any rate that exceeds the intrinsic atrial rate) may be used as a control. Suddenly changing to a "test pacing regimen" such as dual pacing and sensing (DDD) BiV at an AV delay of 100 ms will allow assessment of hemodynamic improvement with BiV pacing. The sudden change is especially useful because cardiac output changes will change the blood pressure almost immediately before peripheral resistance changes the load. With rapid transitions the blood pressure changes reflect changes in cardiac output.

A control is especially valuable when comparing various pacing regimens. Using a control reference provides a stable hemodynamic reference even though the patient's peripheral resistance may be changing over time. This allows for comparing different lead sites on both the RV and the LV or even multiple pacing sites, as may be provided by multielectrode leads to achieve multisite pacing, or comparing a whole range of different AV delays.

PPG signals are particularly robust and relatively easy to obtain and highly reproducible. This makes estimating hemodynamics relatively quick and easy. The use of a control as mentioned above improves accuracy and sensitivity.

In an embodiment, automated search algorithms may be used to iteratively perform hill climbing techniques or binary searches or other search methods to choose a preferred pacing parameter set.

When performing rapid step changes in heart rate, the peripheral resistance does not have time to adjust and this allows for choosing an optimal heart rate relative to the control.

Exemplary Implantable System

Figure 3:
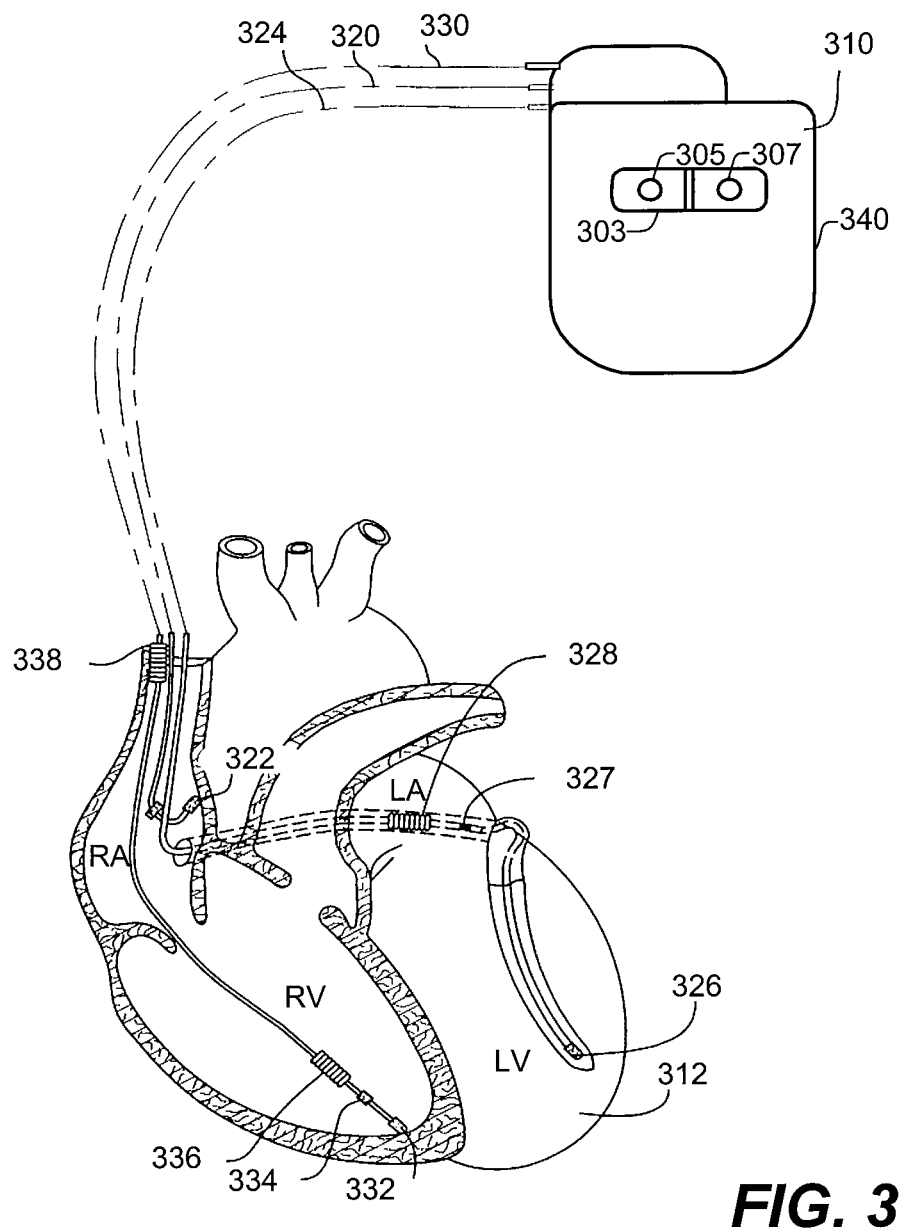
FIG. 3 illustrates an exemplary implantable cardiac stimulation device which can be used to perform various embodiments of the present invention.
Figure 4:
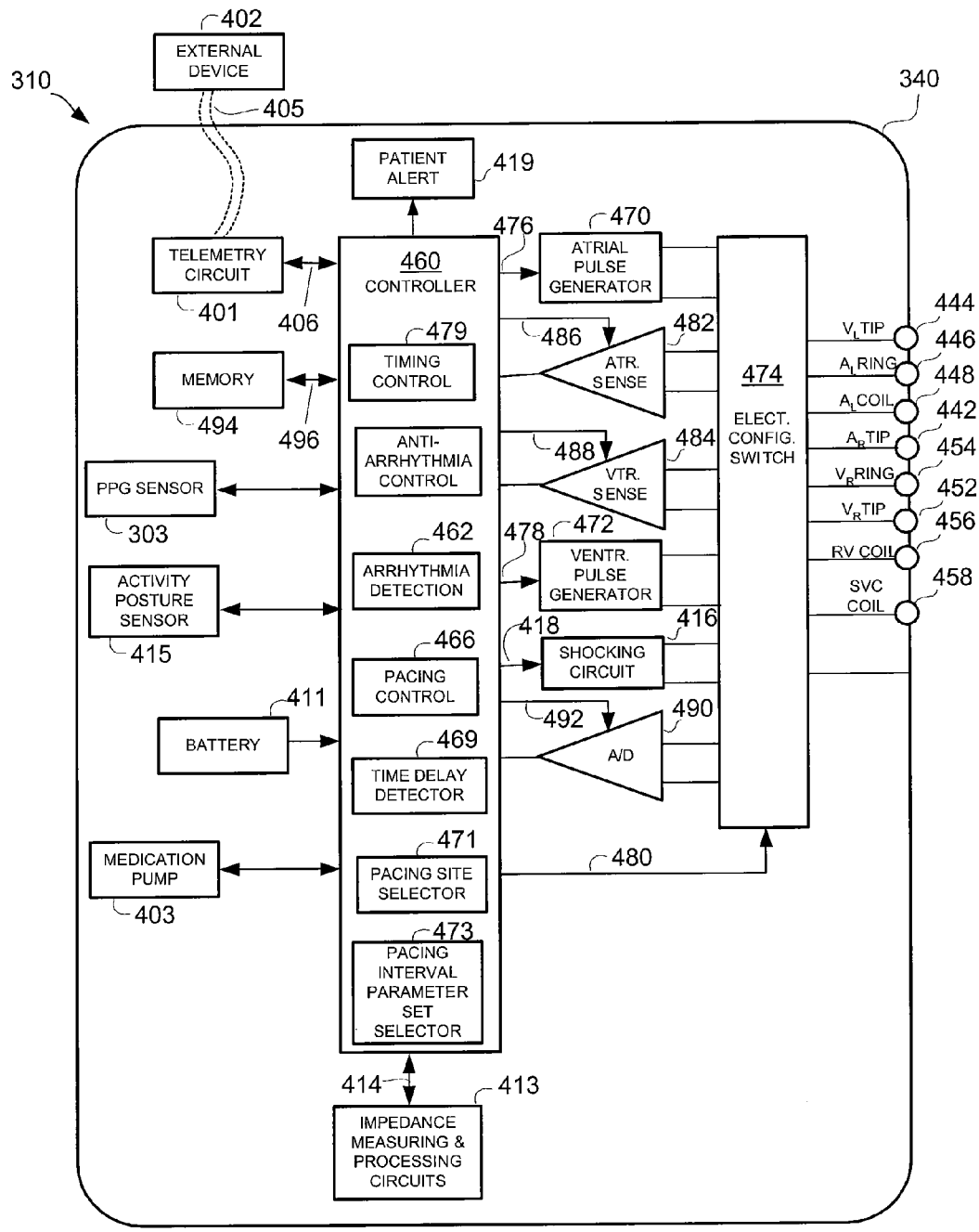
FIG. 4 is a simplified block diagram that illustrates possible components of the implantable device shown in FIG. 3.

FIGS. 3 and 4 will now be used to describe an exemplary implantable system that can be used to implement embodiments of the present invention including but not limited to monitoring, and using, a time delay between a feature of signal indicative of electrical activity of a patient's heart and a feature of a plethysmograph signal indicative of arterial blood volume changes. Referring to FIG. 3, the implantable system is shown as including an implantable stimulation device 310, which can be a pacing device and/or an implantable cardioverter defibrillator. The device 310 is shown as being in electrical communication with a patient's heart 312 by way of three leads, 320, 324 and 330, which can be suitable for delivering multi-chamber stimulation and shock therapy. The leads can also be used to obtain IEGM and/or IPG signals, for use in embodiments of the present invention. As described below, it is also possible that one of these leads (or another lead) can include an optical sensor (also referred to as a PPG sensor) that is useful for obtaining a PPG signal, similar to signal 204 shown in FIG. 2A. Alternatively, the IEGM, EGM, IPG or PPG sensors can be separate from device 310.

In FIG. 3, the implantable device 310 is shown as having a PPG sensor 303 (also referred to as an optical sensor) attached to its housing 340. The PPG sensor 303, which can be used to obtain a PPG signal similar to signal 204 shown in FIG. 2, includes a light source 305 and a light detector 307. The light source 305 can include, e.g., at least one light-emitting diode (LED), incandescent lamp or laser diode, but is not limited thereto. The light detector 307 can include, e.g., at least one photoresistor, photodiode, phototransistor, photodarlington or avalanche photodiode, but is not limited thereto. Light detectors are often also referred to as photodetectors or photocells.

The light source 305 outputs light that is reflected or back-scattered by surrounding patient tissue, and reflected/back-scattered light is received by the light detector 307. In this manner, changes in reflected light intensity are detected by the light detector, which outputs a signal indicative of the changes in detected light. The output of the light detector can be filtered and amplified. The signal can also be converted to a digital signal using an analog to digital converter, if the PPG signal is to be analyzed in the digital domain. A PPG sensor can use a single wavelength of light, or a broad spectrum of many wavelengths. Additional details of exemplary implantable PPG sensors are disclosed in U.S. Pat. No. 6,409,675 "Extravascular Hemodynamic Monitor" and U.S. Pat. No. 6,491,639, entitled "Extravascular Hemodynamic Sensor" (both Turcott), which are incorporated herein by reference.

It is generally the output of the photodetector that is used to produce a PPG signal. However, there exist techniques where the output of the photodetector is maintained relatively constant by modulating the drive signal used to drive the light source, in which case the PPG signal is produced using the drive signal, as explained in U.S. Pat. No. 6,731,967, entitled "Methods and Devices for Vascular Plethysmography via Modulation of Source Intensity," (Turcott), which is incorporated herein by reference.

The PPG sensor 303 can be attached to a housing 340 of an implantable device, which as mentioned above can be, e.g., a pacemaker and/or an implantable cardioverter-defibrillator (ICD), or a simple monitoring device. Exemplary details of how to attach a sensor module to an implantable cardiac stimulation device are described in U.S. patent application Ser. No. 10/913,942, entitled "Autonomous Sensor Modules for Patient Monitoring" (Turcott et al.), now U.S. Pat. No. 7,653,434, which is incorporated herein by reference. It is also possible that the PPG sensor 303 be integrally part of the implantable cardiac stimulation device 310. For example, the PPG sensor 302 can be located within the housing 340 of an ICD (and/or pacemaker) that has a window through which light can be transmitted and detected. In a specific embodiment, the PPG sensor 303 has a titanium frame with a light transparent quartz or sapphire window that can be welded into a corresponding slot cut in the housing of the ICD. This will insure that the ICD enclosure with the welded PPG sensor will maintain a hermetic condition.

Where the PPG sensor is incorporated into or attached to a chronically implantable device 310, the light source 305 and the light detector 307 can be mounted adjacent to one another on the housing or header of the implantable device, or on the bottom of the device, or at any other location. The light source 305 and the light detector 307 can be placed on the side of the implantable device 310 that, following implantation, faces the chest wall, and are configured such that light cannot pass directly from the source to the detector. The placement on the side of the device 310 that faces the chest wall maximizes the signal to noise ratio by directing the signal toward the highly vascularized musculature, and shielding the source and detector from ambient light that enters the body through the skin. Alternatively, at the risk of increasing susceptibility to ambient light, the light source 305 and the light detector 307 can be placed on the face of the device 310 that faces the skin of the patient. Other variations are also possible.

In an alternative embodiment, the PPG sensor 303 (or other plethysmography sensor) can be remote from the housing 340 of the device 310, but communicate with the electronics in the device housing 340 via one or more wires, optical fibers, or wirelessly (e.g., using telemetry, RF signals and/or using body fluid as a communication bus medium). This embodiment enables an obtained PPG signal to be indicative of changes in arterial blood volume at a location remote from the patient's heart, where such location is also remote from the device housing 340. If desired, multiple PPG signals can be obtained, e.g., using multiple PPG sensors at different locations.

In another embodiment, optical fibers can be used to transmit light into and detect light from tissue that is remote from the device housing, even though the light source and light detector are located within or adjacent the device housing 340. This embodiment enables an obtained PPG signal to be indicative of changes in arterial blood volume at a location remote from the patient's heart, where such location is remote from the device housing 340, even though the light source 305 and light detector 307 are not remote from the housing. The distal end of the optical fiber(s) associated with the light source can be generally parallel to the distal end of the optical fiber(s) associated with the light detector, so that the light detector detects the portion of light reflected from tissue. Alternatively, the distal end of the optical fiber(s) associated with the light source can generally face the distal end of the optical fiber(s) associated with the light detector, with tissue therebetween, so that the light detector detects the portion of light transmitted through (as opposed to reflected from) the tissue therebetween.

In an embodiment, a PPG sensor can be within or attached to a lead that may extend from a main device housing 340. Accordingly, in this embodiment, a housing of the sensor module is sized to fit within the implantable lead. For example, the PPG can be located proximal from the distal tip of the lead so that the PPG sensor is sufficiently remote from the heart that variations in pulse transmission time are detectable and meaningful. The portion of the lead that is adjacent to a window of the PPG sensor module, where light is to exit and enter, should allow the light to pass in and out of the sensor. Thus, the lead may be transparent, or include its own window, opening, or the like. The lead can including tines for attaching the lead in its desired position, but may include any other type of fixation means (e.g., a pigtail shaped fixation means), or none at all. The lead can also have a suture sleeve that enables the lead to be sutured to patient tissue. Additional details of a lead that includes an optical sensor that can be used to produce a PPG signal are provided in U.S. patent application Ser. No. 11/231,555, entitled "Multi-Wavelength Implantable Oximeter Sensor" (Poore), now U.S. Pat. No. 7,660,616, and U.S. patent application Ser. No. 11/282,198, entitled "Implantable Self Calibrating Optical Sensors" (Poore), now U.S. Pat. No. 7,840,246.

The implantable PPG sensor 303 obtains a PPG signal that after filtering is similar to signal 204 shown in FIG. 2A that pulsates over the cardiac cycle. Modulation of the signal occurs because arteries distend as the pressure wave created by the heart's pumping mechanism reaches the sensor site. Such a signal can be filtered and/or amplified as appropriate, e.g., to remove respiratory affects on the signal, and the like. Additionally, the signal can be digitized using an analog to digital converter.

The PPG sensor can also be external to the implantable medical device. For example, the external PPG sensor can communicate with the implantable medical device or to an external host unit.

For much of above description, it has been assumed that the plethysmography sensor used to produce a plethysmography signal is a PPG sensor. Thus, the plethysmography signal has often been referred to as a PPG signal. However, it should be noted that other types of plethysmography sensors can alternatively be used. Thus, embodiments of the present invention should not be limited to use with PPG sensors and PPG signals. Further, as mentioned above, electrodes of the various leads can be used to obtain an IPG signal, and the IPG signal can be used in place of the PPG signal.

In specific embodiments, the plethysmography signal can be produced using non-radiant methods and devices, including, but not limited to mechanical strain, electrical impedance, or pressure. More specifically, rather than using a PPG sensor that includes a light source and detector, the implanted plethysmography sensor can include a strain gauge, a linear displacement sensor, or an ultrasound transducer, each of which is known in the art. Alternatively, an impedance plethysmography sensor, which is also known in the art, can be used. Details of exemplary implantable sensors that produce an impedance plethysmography signals are disclosed, e.g., in U.S. Pat. No. 4,674,518, entitled "Method and Apparatus for Measuring Ventricular Volume"; U.S. Pat. No. 4,686,987, entitled "Biomedical Method and Apparatus for Controlling the Administration of Therapy to a Patient in Response to Changes in Physiologic Demand" and U.S. Pat. No. 5,334,222, entitled "Cardiac Simulating Apparatus and Method for Heart Failure Therapy" (all to Salo), which are incorporated herein by reference.

Still referring to FIG. 3, to sense atrial cardiac signals and to provide right atrial chamber stimulation therapy, the device 310 is coupled to an implantable right atrial lead 320 having at least an atrial tip electrode 322, which typically is implanted in the patient's right atrial appendage. To sense left atrial and ventricular cardiac signals and to provide left-chamber pacing therapy, the device 310 is coupled to a "coronary sinus" lead 324 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328.

The device 310 is also shown in electrical communication with the patient's heart 312 by way of an implantable right ventricular lead 330 having, in this embodiment, a right ventricular tip electrode 332, a right ventricular ring electrode 334, a right ventricular (RV) coil electrode 336, and an SVC coil electrode 338. Typically, the right ventricular lead 330 is transvenously inserted into the heart 312 so as to place the right ventricular tip electrode 332 in the right ventricular apex so that the RV coil electrode 336 will be positioned in the right ventricle and the SVC coil electrode 338 will be positioned in the superior vena cava. Accordingly, the right ventricular lead 330 is capable of receiving cardiac signals and delivering stimulation in the form of pacing and shock therapy to the right ventricle.

FIG. 4 will now be used to provide some exemplary details of the components of the implantable devices 310. Referring now to FIG. 4, the implantable devices 310, and alternative versions thereof, can include a microcontroller 460. As is well known in the art, the microcontroller 460 typically includes a microprocessor, or equivalent control circuitry, and can further include RAM and/or ROM memory, logic and timing circuitry, state machine circuitry and/or I/O circuitry. Typically, the microcontroller 460 includes the ability to process or monitor input signals (data) as controlled by a program code stored in a designated block of memory. The details of the design of the microcontroller 460 are not critical to the present invention. Rather, any suitable microcontroller 460 can be used to carry out the functions described herein. The use of microprocessor-based control circuits for performing timing and data analysis functions are well known in the art. In specific embodiments of the present invention, the microcontroller 460 performs some or all of the steps associated with determining an interval used to monitor time delay, select pacing interval sets and/or select pacing sites. Additionally, the microcontroller 460 may detect arrhythmias, and select and control delivery of anti-arrhythmia therapy.

Representative types of control circuitry that may be used with embodiments of the present invention include the microprocessor-based control system of U.S. Pat. No. 4,940,052 (Mann et. al.), entitled "Microprocessor Controlled Rate-Responsive Pacemaker Having Automatic Rate Response Threshold Adjustment" and the state-machines of U.S. Pat. No. 4,712,555 (Thornander et al.), entitled "Physiologically Responsive Pacemaker and Method of Adjusting the Pacing Interval Thereof" and U.S. Pat. No. 4,944,298 (Sholder), entitled "Atrial Rate Based Programmable Pacemaker with Automatic Mode Switching Means". For a more detailed description of the various timing intervals used within the pacing device and their inter-relationship, see U.S. Pat. No. 4,788,980 (Mann et. al.), entitled "Pacemaker Having PVC Response and PMT Terminating Features". The '052, '555, '298 and '980 patents are incorporated herein by reference.

Depending on implementation, the device 310 can be capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation. For example, if the implantable device is a monitor that does not provide any therapy, it is clear that many of the blocks shown may be eliminated.

The housing 340, shown schematically in FIG. 4, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 can further include a connector (not shown) having a plurality of terminals, 442, 444, 446, 448, 452, 454, 456, and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 322.

To achieve left atrial and ventricular sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular tip electrode 326, the left atrial ring electrode 327, and the left atrial coil electrode 328, respectively.

To support right ventricle sensing, pacing and shocking, the connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458, which are adapted for connection to the right ventricular tip electrode 332, right ventricular ring electrode 334, the RV coil electrode 336, and the SVC coil electrode 338, respectively.

An atrial pulse generator 470 and a ventricular pulse generator 472 generate pacing stimulation pulses for delivery by the right atrial lead 320, the right ventricular lead 330, and/or the coronary sinus lead 324 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators, or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry 479 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, etc.) by selectively closing the appropriate combination of switches (not shown) as is known in the art.

Atrial sensing circuits 482 and ventricular sensing circuits 484 may also be selectively coupled to the right atrial lead 320, coronary sinus lead 324, and the right ventricular lead 330, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers, or shared amplifiers. The switch 474 determines the "sensing polarity" of the cardiac signal by selectively closing the appropriate switches, as is also known in the art. In this way, the clinician may program the sensing polarity independent of the stimulation polarity.

Each sensing circuit, 482 and 484, preferably employs one or more low power, precision amplifiers with programmable gain and/or automatic gain control, band-pass filtering, and a threshold detection circuit, as known in the art, to selectively sense the cardiac signal of interest. The automatic gain control enables the device 310 to deal effectively with the difficult problem of sensing the low amplitude signal characteristics of atrial or ventricular fibrillation. Such sensing circuits, 482 and 484, can be used to determine cardiac performance values used in the present invention. Alternatively, an automatic sensitivity control circuit may be used to effectively deal with signals of varying amplitude.

The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity, in the appropriate chambers of the heart. The sensing circuits, 482 and 484, in turn, receive control signals over signal lines, 486 and 488, from the microcontroller 460 for purposes of measuring cardiac performance at appropriate times, and for controlling the gain, threshold, polarization charge removal circuitry (not shown), and timing of any blocking circuitry (not shown) coupled to the inputs of the sensing circuits, 482 and 486.

For arrhythmia detection, the device 310 includes an arrhythmia detector 462 that utilizes the atrial and ventricular sensing circuits, 482 and 484, to sense cardiac signals to determine whether a rhythm is physiologic or pathologic. The timing intervals between sensed events (e.g., P-waves, R-waves, and depolarization signals associated with fibrillation) can be classified by the microcontroller 460 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). Additionally, the arrhythmia detector 462 can perform arrhythmia discrimination, e.g., using measures of arterial blood pressure determined in accordance with embodiments of the present invention. The arrhythmia detector 462 can be implemented within the microcontroller 460, as shown in FIG. 4. Thus, this detector 462 can be implemented by software, firmware, or combinations thereof. It is also possible that all, or portions, of the arrhythmia detector 462 can be implemented using hardware. Further, it is also possible that all, or portions, of the arrhythmia detector 462 can be implemented separate from the microcontroller 460.

In accordance with an embodiment of the present invention, the implantable device 310 includes a time delay detector 469, a pacing site selector 471, and a pacing interval parameter set selector 473. The time delay detector 469 can be used determine the time delay between a feature of a signal indicative of electrical activity of a patient's heart and a feature of a plethysmograph signal indicative of arterial blood volume changes using the techniques described above. Such techniques can include detecting a predetermined feature of the plethysmograph signal indicative of cardiac electrical activity, detecting a predetermined feature of the signal indicative of changes in arterial blood volume, and then determining a time delay between the predetermined feature of the signal indicative of cardiac electrical activity and the predetermined feature of the signal indicative of changes in arterial blood volume. Time delay detector 469 can be implemented within the microcontroller 460, as shown in FIG. 4, and can be implemented by software, firmware, or combinations thereof. It is also possible that all or portions of the time delay detector 469 can be implemented separate from microcontroller 460.

The pacing site selector 471 can be used to select a pacing site or combination of pacing sites based on the time delay information produced by the time delay detector 469. The pacing site selector 471 can be associated with logic to reconfigure a multielectrode lead to pace the pacing site and/or combination of pacing sites during testing and for selecting a pacing site or combination of pacing sites from the tested pacing sites and/or combination of pacing sites.

The pacing interval parameter set selector 473 can be used to select a pacing interval set based on time delay information produced by the time delay detector 469, as well as other information. The pacing interval parameter set selector 473 can send the selected information to the pacing control 466. Pacing interval parameter set selector 473 can test multiple pacing interval sets to select a pacing interval parameter set for continuous use. The time delay detector 469, pacing site selector 471 and pacing interval parameter set selector 473 are shown as separate blocks, but can be combined or implemented using any combination of hardware and/or software within or outside the IMD.

The implantable device 310 can also include a pacing controller 466, which can adjust a pacing rate and/or pacing intervals in accordance with embodiments of the present invention. The pacing controller 466 can be implemented within the microcontroller 460, as shown in FIG. 4. Thus, the pacing controller 466 and other blocks can be implemented by software, firmware, or combinations thereof. It is also possible that all, or portions, of the pacing controller 466 can be implemented using hardware. Further, it is also possible that all, or portions, of the pacing controller 466 can be implemented separate from the microcontroller 460.

The implantable device can also include a medication pump 403, which can deliver medication to a patient. Information regarding implantable medication pumps may be found in U.S. Pat. No. 4,731,051 (Fischell), entitled "Programmable Control Means for Providing Safe and Controlled Medication Infusion" and in U.S. Pat. No. 4,947,845 (Davis), entitled "Method of Maximizing Catheter Longevity in an Implantable Medication Infusion System" both of which are incorporated by reference herein.

Still referring to FIG. 4, cardiac signals are also applied to the inputs of an analog-to-digital (A/D) data acquisition system 490. The data acquisition system 490 can be configured to acquire various signals, including but not limited to, IEGM, PPG and IPG signals, convert the raw analog data into a digital signal, and store the digital signals for later processing and/or telemetric transmission to an external device 402. The data acquisition system 490 can be coupled to the right atrial lead 320, the coronary sinus lead 324, and the right ventricular lead 330 through the switch 474 to sample cardiac signals across any pair of desired electrodes.

The data acquisition system 490 can be coupled to the microcontroller 460, or other detection circuitry, for detecting an evoked response from the heart 312 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 460 detects a depolarization signal during a window following a stimulation pulse, the presence of which indicates that capture has occurred. The microcontroller 460 enables capture detection by triggering the ventricular pulse generator 472 to generate a stimulation pulse, starting a capture detection window using the timing control circuitry 479 within the microcontroller 460, and enabling the data acquisition system 490 via control signal 492 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.), entitled "Cardiac Pacer and Method Providing Means for Periodically Determining Capture Threshold and Adjusting Pulse Output Level Accordingly"; U.S. Pat. No. 4,708,142 (Decote, Jr.), entitled "Automatic Cardiac Capture Threshold Determination System and Method"; U.S. Pat. No. 4,686,988 (Sholder), entitled "Pacemaker System and Method for Measuring and Monitoring Cardiac Activity and for Determining and Maintaining Capture"; U.S. Pat. No. 4,969,467 (Callaghan et. al.), entitled "Pacemaker with Improved Automatic Output Regulation"; and U.S. Pat. No. 5,350,410 (Kleks, et. al.), entitled "Autocapture System for Implantable Pulse Generator", which patents are hereby incorporated herein by reference. The type of capture detection system used is not critical to the present invention.

The microcontroller 460 is further coupled to the memory 494 by a suitable data/address bus 496, wherein the programmable operating parameters used by the microcontroller 460 are stored and modified, as required, in order to customize the operation of the implantable device 310 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 312 within each respective tier of therapy. The memory 494 can also store data including information about the time delays, pacing sites, combination of pacing sites, and/or pacing interval parameter sets.

The operating parameters of the implantable device 310 may be non-invasively programmed into the memory 494 through a telemetry circuit 401 in telemetric communication with an external device 402, such as a programmer, transtelephonic transceiver, or a diagnostic system analyzer. The telemetry circuit 401 can be activated by the microcontroller 460 by a control signal 406. The telemetry circuit 401 advantageously allows intracardiac electrograms and status information relating to the operation of the device 310 (as contained in the microcontroller 460 or memory 494) to be sent to the external device 402 through an established communication link 405. The telemetry circuit can also be used to transmit arterial blood pressure data to the external device 402.

For examples of telemetry devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 310 additionally includes a battery 411 which provides operating power to all of the circuits shown in FIG. 4. If the implantable device 310 also employs shocking therapy, the battery 411 should be capable of operating at low current drains for long periods of time, and then be capable of providing high-current pulses (for capacitor charging) when the patient requires a shock pulse. The battery 411 should also have a predictable discharge characteristic so that elective replacement time can be detected.

The implantable device 310 is also shown as including an activity and/or posture sensor 415. Such a sensor 415 can be a simple one dimensional sensor that converts mechanical motion into a detectable electrical signal, such as a back electro magnetic field (BEMF) current or voltage, without requiring any external excitation. Alternatively, the sensor 415 can measure multi-dimensional activity information, such as two or more of acceleration, direction, posture and/or tilt. Examples of multi-dimensional activity sensors include, but are not limited to: the three dimensional accelerometer-based position sensors disclosed in U.S. Pat. No. 6,658,292 (Kroll et al.), entitled "Detection of Patient's Position and Activity Status Using 3D Accelerometer-Based Position Sensor", which is incorporated herein by reference; the AC/DC multi-axis accelerometer disclosed in U.S. Pat. No. 6,466,821 (Pianca et al.), entitled "AC/DC Multi-Axis Accelerometer for Determining Patient Activity and Body Position" which is incorporated herein by reference; and the commercially available precision dual-axis accelerometer model ADXL203 and three-axis accelerometer model ADXL346, both available from Analog Devices of Norwood, Mass.

The implantable device 310 can also include a magnet detection circuitry (not shown), coupled to the microcontroller 460. It is the purpose of the magnet detection circuitry to detect when a magnet is placed over the implantable device 310, which magnet may be used by a clinician to perform various test functions of the implantable device 310 and/or to signal the microcontroller 460 that the external programmer 402 is in place to receive or transmit data to the microcontroller 460 through the telemetry circuits 401.

As further shown in FIG. 4, the device 310 is also shown as having an impedance measuring and processing circuit 413 which is enabled by the microcontroller 460 via a control signal 414 and can be used for obtaining many types of bodily and intracardiac impedances, including a network of single- or multi-vector impedance measurements. Such impedance measurements can be used, e.g., for trending many kinds of physiological variables, and can also be used for detection of air movement in and out of the lungs, blockage of airways, lead impedance surveillance during acute and chronic phases for proper lead positioning or dislodgement; lead integrity by detecting insulation abrasion, operable electrodes, and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 413 may be coupled to the switch 474 so that any desired electrodes may be used, and networks of vectors can be selected. In accordance with an embodiment, the impedance measuring circuit 413 is used to obtain an IPG signal, which can be used in the embodiments described with reference to the flow diagrams of FIGS. 1A and 1B.

In the case where the implantable device 310 is also intended to operate as an implantable cardioverter/defibrillator (ICD) device, it should detect the occurrence of an arrhythmia, and automatically apply an appropriate electrical shock therapy to the heart aimed at terminating the detected arrhythmia. To this end, the microcontroller 460 further controls a shocking circuit 416 by way of a control signal 418. The shocking circuit 416 generates shocking pulses of low (up to 0.5 Joules), moderate (0.5-10 Joules), or high energy (11 to 40 Joules), as controlled by the microcontroller 460. Such shocking pulses are applied to the patient's heart 312 through at least two shocking electrodes, and as shown in this embodiment, selected from the left atrial coil electrode 328, the RV coil electrode 336, and/or the SVC coil electrode 338. As noted above, the housing 340 may act as an active electrode in combination with the RV electrode 336, or as part of a split electrical vector using the SVC coil electrode 338 or the left atrial coil electrode 328 (i.e., using the RV electrode as a common electrode).

The above described implantable device 310 was described as an exemplary pacing device. One or ordinary skill in the art would understand that embodiments of the present invention can be used with alternative types of implantable devices. Accordingly, embodiments of the present invention should not be limited to use only with the above described device.

Embodiments of the present invention have been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 1A and 1B. Further, it is possible to change the order of some of the steps shown in FIGS. 1A and 1B, without substantially changing the overall events and results. For another example, it is possible to change the boundaries of some of the blocks shown in FIG. 4.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

The invention claimed is:

1. A method of selecting a pacing site or a combination of pacing sites at which to deliver cardiac stimulation to a patient, the method comprising:
(a) for each of a plurality of pacing sites and/or combinations of pacing sites within the patient
   (a.1) using the pacing site or the combination of pacing sites to deliver cardiac stimulation;
   (a.2) obtaining a signal indicative of electrical activity of the patient's heart while the pacing site or the combination of pacing sites is being used to deliver cardiac stimulation;
   (a.3) obtaining a plethysmograph signal indicative of changes in arterial blood volume while the pacing site or the combination of pacing sites is being used to deliver cardiac stimulation; and
   (a.4) determining a time delay between a predetermined feature of the signal indicative of electrical activity and a predetermined feature of the plethysmograph signal indicative of changes in arterial blood volume; and
(b) selecting a pacing site or a combination of pacing sites from the plurality of pacing sites and/or combinations of pacing sites based on the time delays.

2. The method of claim 1 implemented using an implantable lead having a plurality of electrodes each corresponding to a different pacing site within the patient, said method further comprising:
repeating steps (a) and (b) from time to time to select a current preferred pacing site or a current preferred combination of pacing sites each time steps (a) and (b) are repeated; and
each time steps (a) and (b) are repeated activating the one or more electrodes that correspond to the current preferred pacing site or the current preferred combination of pacing sites selected at step (b) for stimulation delivery.

3. The method of claim 1, wherein the plurality of pacing sites and/or combination of pacing sites are obtained by moving one or more electrodes interoperatively.

4. The method of claim 1, wherein step (b) comprises one of the following:
   (b.1) selecting the pacing site or the combination of pacing sites that corresponds to the shortest of the time delays determined at step (a);
   (b.2) selecting the pacing site or the combination of pacing sites that corresponds to the shortest of the time delays determined at step (a) at which phrenic nerve stimulation did not occur;
   (b.3) selecting the pacing site or combination of pacing sites based on a function using the time delay determined at step (a) and an amplitude of the plethysmograph signal indicative of changes in arterial blood volume; and
   (b.4) selecting any one of the pacing sites or the combination of pacing sites that corresponds to any one of the time delays that meet a predetermined criteria.

5. The method of claim 1, wherein:
step (a.2) comprises obtaining one of an intracardiac electrogram (IEGM), a subcutaneous electrocardiogram (subQ ECG), and surface electrocardiogram (surface ECG) while the pacing site or the combination of pacing sites is being used to deliver cardiac stimulation;
step (a.3) comprises obtaining one of a photoplethysmography (PPG) signal and an impedance plethysmography (IPG) signal while the pacing site or combination of pacing sites is being used to deliver cardiac stimulation; and
step (a.4) comprises
   (a.4.1) detecting a predetermined feature indicative of ventricular depolarization of the one of the IEGM, the subQ ECG and the surface ECG;
   (a.4.2) detecting a predetermined feature of the one of the PPG signal and the IPG signal; and (a.4.3) determining the time delay between the predetermined feature indicative of ventricular depolarization and the predetermined feature of the one of the PPG signal and the IPG signal.

6. The method of claim 1, wherein the predetermined feature of the plethysmograph signal indicative of changes of arterial blood volume comprises one of:
   a minimum amplitude;
   a maximum upward slope;
   a maximum amplitude;
   a maximum downward slope; and
   a dicrotic notch.

7. The method of claim 1, wherein the cardiac stimulation is delivered to provide cardiac resynchronization therapy (CRT).

8. The method of claim 1, wherein the plethysmograph signal is obtained using a plethysmograph sensor that is at least 1 cm remote from the pacing site or combination of pacing sites.

9. The method of claim 1, wherein step (b) comprises selecting the pacing site or the combination of pacing sites that corresponds to the shortest of the time delays determined at step (a).

10. A method of selecting a pacing interval parameter set for use when delivering cardiac stimulation to a patient, the method comprising:
   (a) for each of a plurality of pacing interval parameter sets
       (a.1) using the pacing interval parameter set to deliver cardiac stimulation;
       (a.2) obtaining a signal indicative of electrical activity of the patient's heart while the pacing interval parameter set is being used to deliver cardiac stimulation;
       (a.3) obtaining a plethysmograph signal indicative of changes in arterial blood volume while the pacing interval parameter set is being used to deliver cardiac stimulation; and
       (a.4) determining a time delay between a predetermined feature of the signal indicative of electrical activity and a predetermined feature of the plethysmograph signal indicative of changes in arterial blood volume; and
   (b) selecting a pacing interval parameter set from the plurality of pacing interval parameter sets based on the time delays.

11. The method of claim 10, wherein each pacing interval parameter set includes at least one pacing interval parameter, with an initiating event being either a delivered pacing pulse or a sensed depolarization.

12. The method of claim 11, wherein each pacing interval parameter set includes at least one of the following pacing interval parameters:
   atrio-ventricular (AV) delay;
   interventricular (VV) delay;
   interatrial (AA) delay; and
   intraventricular delay.

13. The method of claim 10, wherein step (b) comprises one of the following:
   (b.1) selecting the pacing interval parameter set that corresponds to the shortest of the time delays determined at step (a);
   (b.2) selecting the pacing interval parameter set that corresponds to the shortest of the time delays determined at step (a) at which phrenic nerve stimulation did not occur;
   (b.3) selecting a pacing interval set based on a function using the time delay determined at step (a) and an amplitude of the plethysmograph signal indicative of changes in arterial blood volume; and
   (b.4) selecting any one of the pacing interval parameter set that corresponds to any one of the time delays that meet a predetermined criteria.

14. The method of claim 10, wherein:
   step (a.2) comprises obtaining one of an intracardiac electrogram (IEGM), a subcutaneous electrocardiogram (subQ ECG), and surface electrocardiogram (surface ECG) while the pacing interval parameter set is being used to deliver cardiac stimulation;
   step (a.3) comprises obtaining one of a photoplethysmography (PPG) signal and an impedance plethysmography (IPG) signal while the pacing interval parameter set is being used to deliver cardiac stimulation; and
   step (a.4) comprises
       (a.4.1) detecting a predetermined feature indicative of ventricular depolarization of the one of the IEGM, the subQ ECG and the surface ECG;
       (a.4.2) detecting a predetermined feature of the one of the PPG signal and the IPG signal; and
       (a.4.3) determining the time delay between the predetermined feature indicative of ventricular depolarization and the predetermined feature of the one of the PPG signal and the IPG signal.

15. The method of claim 10, wherein the predetermined feature of the plethysmograph signal indicative of changes of arterial blood volume comprises one of:
   a minimum amplitude;
   a maximum upward slope;
   a maximum amplitude;
   a maximum downward slope; and
   a dicrotic notch.

16. The method of claim 10, wherein the cardiac stimulation is delivered to provide cardiac resynchronization therapy (CRT).

17. The method of claim 10, wherein the plethysmograph signal is obtained using a plethysmograph sensor that is at least 1 cm remote from the pacing site or combination of pacing sites.

18. The method of claim 10, wherein step (b) comprises selecting the pacing interval parameter set from the plurality pacing interval sets that corresponds to the shortest of the time delays determined at step (a).

* * * * *